United States Patent [19]

Komiya

[11] 4,043,323
[45] Aug. 23, 1977

[54] MEDICAL INSTRUMENT ATTACHED TO AN ENDOSCOPE

[75] Inventor: Osamu Komiya, Hachioji, Japan

[73] Assignee: Olympus Optical Co., Ltd., Tokyo, Japan

[21] Appl. No.: 643,861

[22] Filed: Dec. 23, 1975

[30] Foreign Application Priority Data

Dec. 27, 1974  Japan ..................................... 49-274

[51] Int. Cl.² ................................................. A61B 1/00
[52] U.S. Cl. ........................................................ 128/4
[58] Field of Search ........................................ 128/3–8, 128/303 R, 303.15; 294/16, 69, 28, 118, 115; 188/65.1, 67; 74/527, 529; 119/153, 154

[56] References Cited

U.S. PATENT DOCUMENTS

| 3,854,473 | 12/1974 | Matsuo ..................................... 128/8 |
| 3,897,775 | 8/1975 | Furihata ................................... 128/6 |

FOREIGN PATENT DOCUMENTS

| 1,275,326 | 8/1968 | Germany ............................. 119/153 |
| 49,750 | 11/1931 | Norway ................................ 119/154 |

*Primary Examiner*—Robert W. Michell
*Assistant Examiner*—Henry S. Layton

[57] ABSTRACT

A medical instrument such as forceps attached to an endoscope, wherein a base member is provided at the base end of the forceps; a slider connected by wire to a movable head fitted to the tip of the forceps is slidably mounted on a base member provided at the base end of the forceps; a bore formed in the slider contains a pawl, and a spring and stem both cooperating in urging the pawl for engagement with toothed portions formed on the base member; when the knob portion of the stem projecting outward from the bore is depressed, then the pawl is disengaged from the toothed portions and as the result, the knob portion is so actuated as to tilt the stem sideways for latching, thereby keeping the pawl in a disengaged position, and allowing the slider freely to slide over the base member.

6 Claims, 7 Drawing Figures

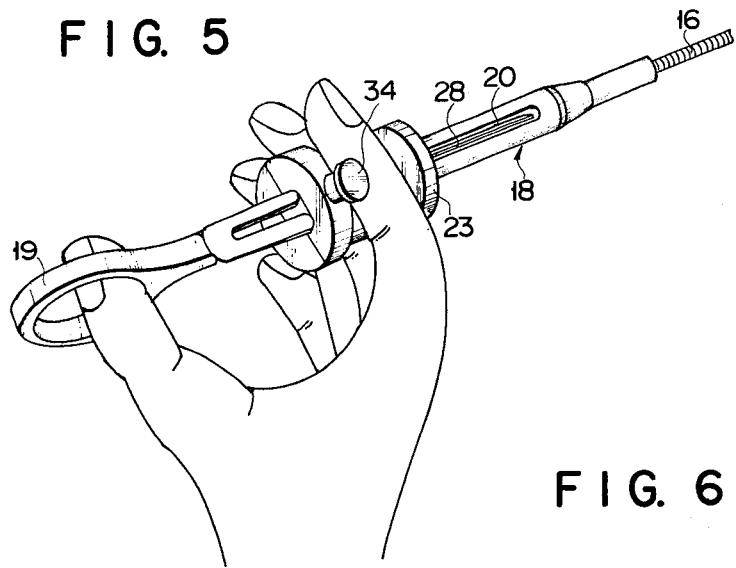
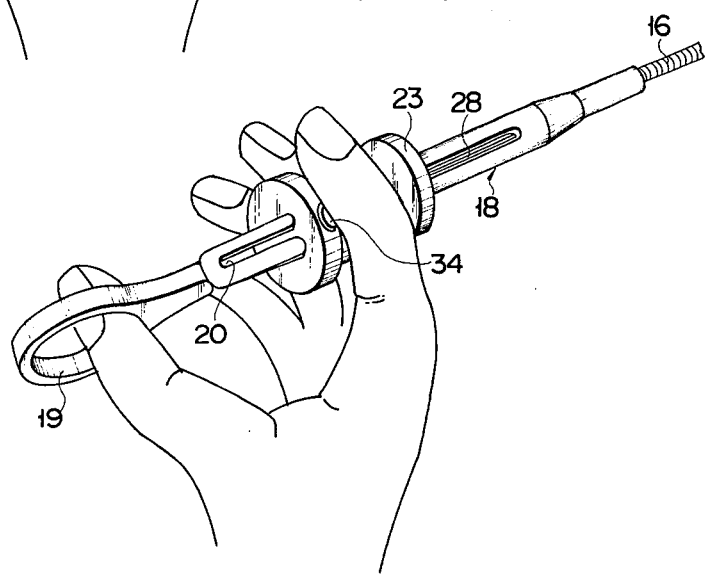
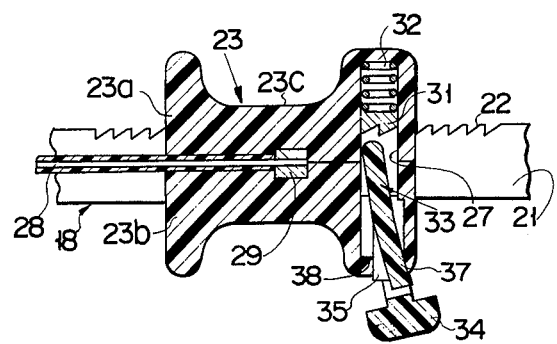

MEDICAL INSTRUMENT ATTACHED TO AN ENDOSCOPE

BACKGROUND OF THE INVENTION

This invention relates to improvements on a medical instrument, for example, forceps attached to an endoscope and inserted therewith into the body cavity of human beings.

Various medical treatments have been carried out, as is well known, by conducting a medical instrument, for example, forceps into the body cavity of human beings through a channel specifically formed in an endoscope during observation of an effected portion appearing in said body cavity. A medical instrument attached to the endoscope generally comprises an elongate flexible tube; a movable head supported at the tip of said flexible tube; forceps having a pair of cutting cups; a base member disposed at the base end of the flexible tube, designed to be gripped by operator's fingers and provided with a ring-shaped finger hook; an actuating wire inserted into the flexible tube so as to slide lengthwise thereof, having its forward end operatively connected to the movable head and actuating the movable head by sliding relative to the flexible tube; and a slider fitted with the base end of the actuating wire and mounted on the base member so as to slide lengthwise thereof so as to cause the sliding of said wire. The medical instrument is conducted into the human body cavity through the endoscope channel with the movable head kept foremost.

Hitherto, it has been necessary for an operator to manipulate the medical instrument by one of his hands while operating an endoscope by the other hand for observation. In the case of forceps, the operator had to move the slider relative to the base member by inserting the thumb of said one hand into the ring-shaped finger hook of the base member and gripping the slider by the forefinger and middle finger of said one hand, thereby actuating a pair of cups disposed at the tip of the flexible tube.

The prior art forceps were provided with a locking mechanism which included a toothed portion formed lengthwise of the base member, a pawl supported on the slider for engagement with said toothed portion and a spring for urging the pawl toward said toothed portion.

With the conventional locking mechanism, the operator had to keep the pawl disengaged from the toothed portion against the force of a spring while moving the slider free from the base member. Such one hand-operation of the medical instrument was accompanied with considerable difficulties and failed to render said operation very accurate.

SUMMARY OF THE INVENTION

It is accordingly the object of this invention to provide such a medical instrument attached to an endoscope as is free from the drawbacks of the prior art medical instrument and capable of allowing the operator to lock and release a locking mechanism accurately and easily by a single hand.

The medical instrument of this invention is provided with latch means for locking the pawl means of a locking mechanism in a state disengaged from the toothed portions of a base member. When the operator depresses by hand a knob portion formed on the pawl means to tilt the pawl means sideways, then the latch means keeps the pawl means in a disengaged position, enabling the operator to move the slider freely without applying an appreciable amount of force to the fingers. Where the knob portion is tilted slightly in the opposite direction to lock the slider at a desired position, then the latch means is readily released, enabling the slider to be quickly locked exactly at any specified point on the base member.

BRIEF DESCRIPTION OF THE DRAWING

FIGS. 5 and 6 illustrate the manner in which the operator manipulates the medical instrument of the invention by fingers; and FIG. 7 indicates the operation of the latch means, showing part of FIG. 2 in section.

DESCRIPTION OF THE PREFERRED EMBODIMENTS

Figure 1:
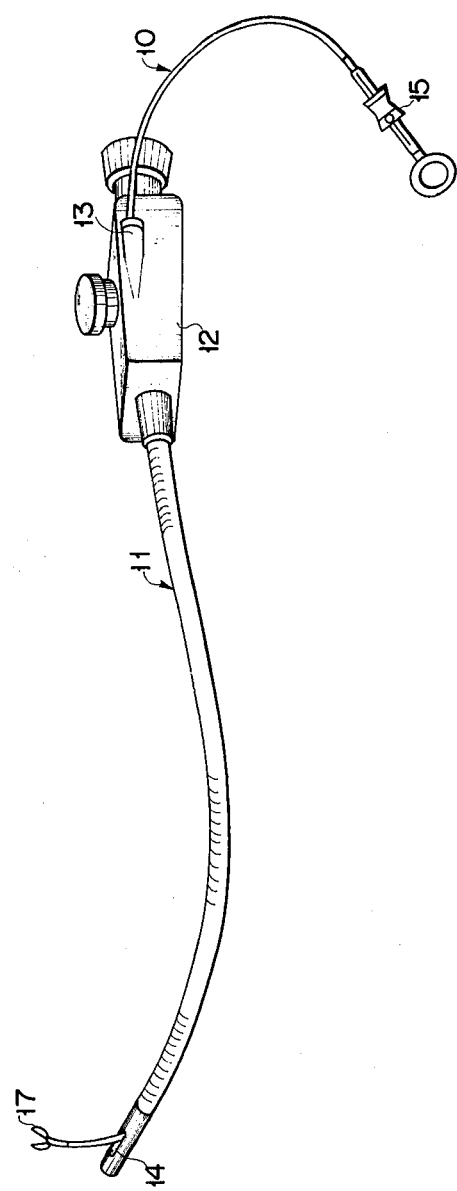
FIG. 1 shows the medical instrument of this invention passed through an endoscope for practical application.
Figure 2:
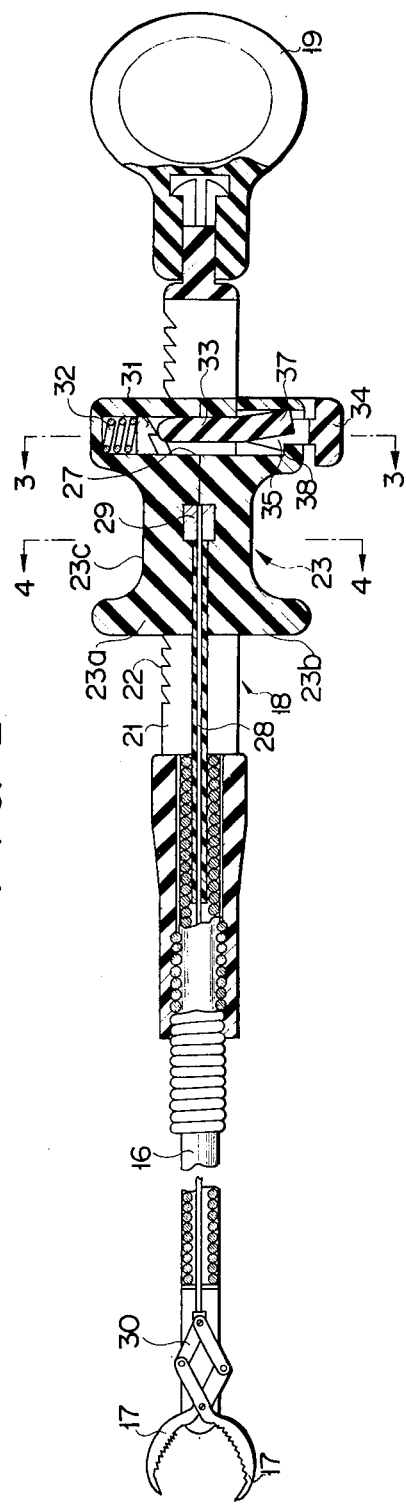
FIG. 2 is an axial or longitudinal sectional view, partly exploded, of the medical instrument of this invention shown in FIG. 1, particularly showing the detailed arrangement of the latch means.

In this embodiment, the medical instrument is formed of, for example, forceps. As shown in FIG. 1, the forceps 10 are brought into the body cavity of a human being in a state inserted into the known endoscope 11. Namely, the forceps 10 are let to pass through the specific channel of an endoscope 11 at an inlet 13 formed in the control unit 12 of said endoscope 11 with the tip of the forceps 10 kept foremost. Said tip is made to project outward from an opening 14 formed at the distal end of a flexible tube 16 (FIG. 2). Said projection is effected by an operator manipulating with one hand a manual control section 15 provided at the base end of the forceps 10, while observing the human body cavity by an endoscope 11 placed therein.

Figure 3:
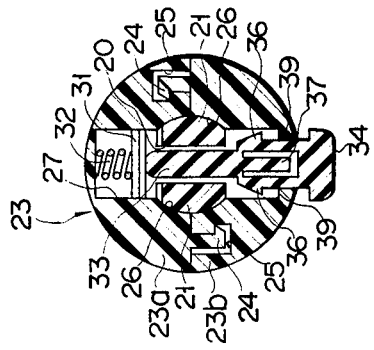
FIGS. 3 and 4 are sectional views on line 3—3 and line 4—4 of FIG. 2.
Figure 4:
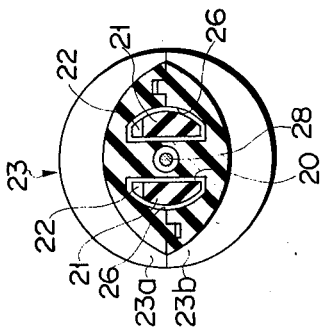

Referring to FIG. 2, the elongate flexible tube 16 of the forceps 10 is formed of a closely wound coil and a plastics tube mounted thereon. The tip of said flexible tube 16 is fitted with a pair of freely operative cutting cups 17 collectively constituting a movable head. The base end of the flexible tube 16 is provided with a base member 18 forming part of the manual control section 15. One end of the base member 18 is fitted with a ring-shaped finger hook 19 to be gripped by the thumb of one hand of the operator. Said finger hook 19 is made to rotate about the axis of the base member 18. The base member 18 includes a pair of guide rods 21 axially extending in parallel to define a similarly lengthwise extending long groove 20 and toothed portions 22 formed on the lateral edges of said guide rods 21 positioned on the same side. The paired guide rods 21 of the base member 18 are fitted with a slider 23 constituting part of the manual control section 15, said slider 23 being made to slide axially of the guide rods 21. As seen from FIGS. 3 and 4, the slider 23 is splittable into a pair of upper and lower plastics members 23a, 23b of the same shape. Said members 23a, 23b are coupled together by means of a projection 24 and engagement hole 25 provided on each of the facing surfaces of said paired members 23a, 23b. When engaged with each other, said paired members 23a, 23b define axially extending engagement holes 26 into which the guide rods 21 are slidably fitted. A radially or crosswise extending bore 27 is formed in an open end of the slider 23. The periphery of the slider 23 is provided with a grip section 23c to be easily held by the other fingers of said one hand of the operator than the thumb.

The two paired members 23a, 23b of the slider 23 are coupled together by fixing the base end of an elongate actuating wire 28 at a point 29. The actuating wire 28 is inserted into the flexible tube 16 so as to slide axially therethrough. The forward end of said actuating wire 28 is operatively connected to the paired cutting cups 17 through the known link mechanism 30. The link mechanism 30 is so designed as to cause the paired cups 17 to be opened when the actuating wire 28 is pushed to the left of FIG. 2 and to be closed when said wire is pulled to the right. Like the ordinary forceps, said paired cups 17 pick up an affected tissue of the human body cavity.

In the radial bore 27 of the slider 23, a pawl 31 faces the toothed portions 22 of the base member 18 for engagement therewith. The pawl 31 is normally urged toward the toothed portions 22 for engagement therewith by means of a coil spring 32. A stem 33 is inserted into the radial bore 27. The inserted end of the stem 33 contacts the pawl 31 and the other end portion of said stem 33 extending outward from the bore 27 terminates with a knob portion 34 manipulated by the fingers of an operator. When the knob portion 34 is manually depressed by the operator, the pawl 31 is disengaged from the toothed portions 22 against the force of the coil spring 32, enabling the slider 23 freely to slide over the base member 18. When the operator releases his fingers to bring the stem 33 back to its original position, then the pawl 31 again engages the toothed portions 22, causing the slider 23 to be locked to the base member 18. Namely, the toothed portions 22, pawl 31 and stem 33 jointly constitute a locking mechanism for releasably locking the slider 23 to the base member 18. With this embodiment, the pawl 31 and stem 33 are formed of separate parts, but may be formed integrally with each other. Said pawl 31 and stem 33 constitute pawl means capable of being engaged with the toothed portions 22 and disengaged therefrom.

The stem 33 is designed to move radially through the bore 27 and also to be tilted axially through a small angle. The stem 33 is formed of suitable plastics material. With the stem 33, a shoulder portion 35 is formed on one lateral side; a projection 36 is provided on each of the two opposite lateral sides disposed at right angles to said one lateral sides; and a tongue 37 is provided at the center of one lateral side opposite to the first mentioned one lateral side, all these attachments being formed integrally with the stem 33. Stepped portions 38, 39 are formed integrally with the inner walls of the bore 27. The stepped portion 38 faces the shoulder portion 35 of the stem 33, both portions constituting latch means. Two stepped portions 39 face a pair of projections 36, both projections and stepped portions constituting the later described removal-preventing means. The tongue 37 forms the later described another urging means in cooperation with the inner walls of the bore 27.

There will be described by reference to FIG. 2 the operation of the forceps 10 of this invention constructed as described above. FIG. 2 shows the shoulder portion 35 of the stem 33 latched to the stepped portion 38. The stem 33 urges the inner end of the pawl 31 against the force of the spring 32 to keep the pawl 31 disengaged from the toothed portions 22. Under this condition, the slider 23 is left free with respect to the base member 18, enabling the operator to move the slider 23 to a desired point. When the slider 23 is carried to the left of FIG. 2, the paired cups 17 are closed.

Where it is desired to lock the slider 23 to the base member 18 after moving it for a certain distance, then the operator pushes the knob portion 34 of the stem 33 sideways, as illustrated in FIG. 5, with the forefinger to tilt the stem 33, causing the shoulder portion 35 to be disengaged from the stepped portion 38. As the result, the pawl 31 quickly engages the toothed portions 22, as shown in FIG. 7, by means of the spring 32, causing the slider 23 to be locked in a state in capable of sliding over the base member 18. In this case, each tooth of the toothed portions 22 has a serrated form in which one side of the tooth is inclined. Where, therefore, the slider 23 is forthfully pulled to the right of FIG. 7, then the pawl 31 rides over one tooth after another of the toothed portions 22 against the force of the coil spring 32, allowing the slider 23 to slide to the right one step each time over the base member 18. However, the slider 23 can not be carried to the left at all due to said serrated form of the teeth of the toothed portions 22.

As used herein, the term "lock" shows that the base member 18 is prevented from sliding in one or both directions. It is possible to use the toothed portions 22 whose teeth each have a rectangular form in which both lateral sides project and shape the pawl 32 into such form as engages said rectangular tooth, thereby allowing the slider to slide over the base member in both directions. This arrangement may be used with the medical instrument of this invention in place of the foregoing embodiment.

Where the shoulder portion 35 is released from the stepped portion 38 as mentioned above, then the stem 33 is quickly urged by the spring 32 with a tendency to slip out of the bore 27. Since, however, the paired projections 36 of the stem 33 abut against the corresponding stepped portions 39, the stem 33 is not likely at all to be thrown out of the bore 27.

Where it is desired to move the slider 23 again, the operator depresses the knob portion 34, as shown in FIG. 6, with the forefinger against the force of the spring 32. While being depressed, the knob 34 is moved sideways to tilt the stem 33. Then the stem 33 is brought into a latched condition shown in FIG. 2 to keep the pawl 31 released. Thereafter, the operator can move the slider 23 with his fingers detached from the knob portion 34.

The tongue 37 formed integrally with the stem 33 flexibly projects, as shown in FIG. 2, obliquely sideways relative to the longitudinal direction of the stem 33. The end of the tongue 37 resiliently abuts against the inner wall of the bore 27. This resilient abutment causes the stem 33 to be urged in a tilting direction in which the shoulder portion 35 of the stem 33 is latched to the stepped portion 38, thereby attaining the tighter latching of the shoulder portion 35 to the stepped portion 38. The urging action of the tongue 37 offers the advantage that when the operator depresses the stem 33 further downward from the condition of FIG. 7, the stem 33 is naturally tilted to attain latching. However, the latching means used with the medical instrument of this invention can well serve the purpose, even if the stem 33 is not provided with the above-mentioned tongue 37.

The operator has to touch the knob portion 34 only once in locking the slider 23 to the base member 18 or releasing the slider 23 therefrom.

With the foregoing embodiment, the medical instrument was formed of, for example, forceps. However, this invention is not limited thereto, but may also be applicable to any other type of medical instrument, provided it can be inserted into the human body cavity together with an endoscope. Therefore, the movable head fitted to the tip of the medical instrument may be replaced by any other form of body cavity-treating means.

What is claimed is:

1. A medical instrument attached to an endoscope for insertion into a body cavity of a human being together with said endoscope, said instrument having a movable head attached to an elongate flexible tube; said movable head fitted to one end of said flexible tube; a base member disposed at the other end of the flexible tube and provided with a finger hook to be gripped by one of the fingers of an operator; an actuating wire inserted into the flexible tube so as to be slidable therethrough in the longitudinal direction and having its forward end operatively connected to the movable head, a slider fitted with the base end of the actuating wire, mounted on the base member so as to be slidable lengthwise of the base member, thereby causing the sliding of said actuating wire and further provided with a finger-grip portion; and a manually operative locking mechanism for releasably locking the slider at a desired point on the base member, the improvement being that the locking mechanism includes a toothed portion formed on one lateral edge of the base member in the longitudinal direction thereof; locking means received in a bore formed in the slider so as to be movable therein in a direction transverse to said longitudinal direction, said locking means having a knob portion extending outward from the bore of the slider and being designed to engage the toothed portion of the base member; and urging means supported on the slider so as to normally urge the locking means into engagement with the toothed portion of the base member, said locking means being disengaged from the toothed portion by depressing the knob portion against the action of said urging means; said locking means also being tiltable through an angle in a direction away from said transverse direction and having latch means for latching said locking means in a depressed position in which said locking means has been disengaged from the toothed portion of the base member when said locking means is tilted through said angle.

2. The medical instrument according to claim 1, which comprises another urging means for normally urging the locking means to be tightly latched by the latch means.

3. The medical instrument according to claim 1, wherein said locking means is received in the bore of the slider to face the toothed portion of the base member for engagement therewith and includes a pawl normally urged toward the toothed portion for engagement therewith and a stem, one end of which abuts against the pawl, and the other end of which projects outward from the bore of the slider and terminates in said knob portion.

4. The medical instrument according to claim 3, wherein the latch means includes a shoulder formed integrally with the stem and a stepped portion formed on the inner wall of the bore of the slider to face the stepped portion for engagement therewith.

5. The medical instrument according to claim 4, wherein the stem is formed of plastics material and said latching means has a tongue formed integrally therewith, said tongue resiliently abutting against the inner wall of the bore of the slider to cause the shoulder of the stem to be tightly latched to the stepped portion of the slider.

6. The medical instrument according to claim 3, wherein removal-preventing means is provided between the slider and stem to prevent the stem from being thrown out of the bore of the slider.

* * * * *